United States Patent
Zeidler et al.

[11] Patent Number: 5,827,332
[45] Date of Patent: Oct. 27, 1998

[54] AZO DYES AND A METHOD OF MAKING A HYDROCARBON USING AN AZO DYE

[75] Inventors: Georg Zeidler, Dannstadt-Schauernheim; Gerhard Scholz, Ludwigshafen; Claudia Kräh, Mutterstadt; Karin Heidrun Beck, Ludwigshafen; Udo Mayer, Frankenthal, all of Germany

[73] Assignee: BASF Aktiengesellschaft, Ludwigshafen, Germany

[21] Appl. No.: 647,899

[22] PCT Filed: Dec. 9, 1994

[86] PCT No.: PCT/EP94/04091

§ 371 Date: Jun. 6, 1996

§ 102(e) Date: Jun. 6, 1996

[87] PCT Pub. No.: WO95/17483

PCT Pub. Date: Jun. 29, 1995

[30] Foreign Application Priority Data

Dec. 22, 1993 [DE] Germany ............... 43 43 823.7

[51] Int. Cl.[6] ............... C10L 1/22; C10L 1/04; C09B 29/095; C09B 29/085; G09B 21/053
[52] U.S. Cl. ............... 44/328; 208/12; 208/15; 208/16; 534/797; 534/802; 534/804; 534/832; 534/831; 534/843; 534/851; 534/876; 534/852; 534/860; 534/DIG. 1
[58] Field of Search ............... 534/797, 802, 534/804, 832, 851, 852, 860, 876, 831, 843, DIG. 1; 44/328; 208/12, 15, 16

[56] References Cited

U.S. PATENT DOCUMENTS

| | | | |
|---|---|---|---|
| 3,218,309 | 11/1965 | Elslager et al. | 534/753 X |
| 4,011,209 | 3/1977 | Defeo et al. | 534/856 X |
| 4,037,007 | 7/1977 | Wood | 428/199 |
| 4,186,243 | 1/1980 | Astbury et al. | 428/537 |
| 4,268,439 | 5/1981 | Kruckenberg | 534/856 X |
| 4,315,756 | 2/1982 | Zeidler et al. | 44/59 |
| 4,840,884 | 6/1989 | Mooberry et al. | 430/557 |
| 4,904,765 | 2/1990 | Derber et al. | 534/573 |
| 5,247,071 | 9/1993 | Hansen et al. | 534/596 |
| 5,266,227 | 11/1993 | Reichelt et al. | 534/851 X |
| 5,364,745 | 11/1994 | Mooberry et al. | 430/359 |

FOREIGN PATENT DOCUMENTS

| | | | |
|---|---|---|---|
| 0256460 | 2/1988 | European Pat. Off. | 44/59 |
| 0446731 | 9/1991 | European Pat. Off. | 44/59 |
| 0499845 | 8/1992 | European Pat. Off. | 44/59 |
| 0519270 | 12/1992 | European Pat. Off. | 44/59 |
| 0553858 | 8/1993 | European Pat. Off. | 44/59 |
| 2232636 | 1/1975 | France | 44/59 |
| 2254610 | 7/1975 | France | 44/59 |
| 2342168 | 9/1977 | France | 44/59 |
| 3700329 | 7/1988 | Germany | 44/59 |
| 0953719 | 4/1964 | United Kingdom | 44/59 X |
| 1153144 | 5/1969 | United Kingdom | 44/59 |

*Primary Examiner*—Floyd D. Higel
*Attorney, Agent, or Firm*—Oblon, Spivak, McClelland, Maier & Neustadt, P.C.

[57] ABSTRACT

Azo dyes of the formula

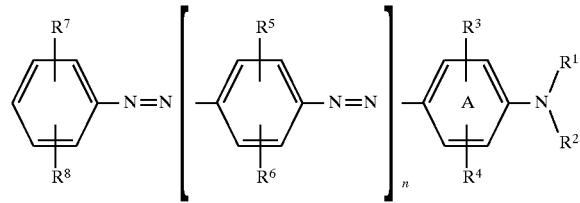

where
  the ring A may be benzofused,
  n is 0 or 1, and $R^1$–$R^8$ are as defined,
as pH-dependent markers for hydrocarbons, hydrocarbons containing the above-mentioned azo dyes, and a method for detecting these azo dyes in hydrocarbons.

2 Claims, No Drawings

AZO DYES AND A METHOD OF MAKING A HYDROCARBON USING AN AZO DYE

This application is a 371 of PCT/EP94/04091 filed Dec. 9, 1994.

BACKGROUND OF THE INVENTION

FIELD OF THE INVENTION

The present invention relates to the use of azo dyes of the formula I

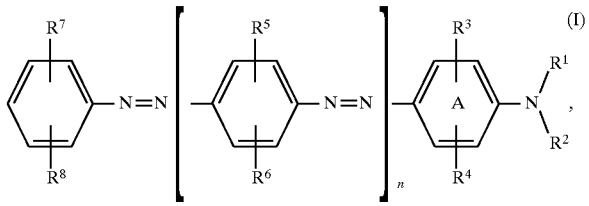

where
  the ring A may be benzofused,
  n is 0 or 1,
  $R^1$ is hydrogen or $C_1$–$C_{15}$-alkyl which may be interrupted by from 1 to 4 ether oxygen atoms,
  $R^2$ is $C_1$–$C_{15}$-alkyl which may be interrupted by from 1 to 4 ether oxygen atoms, or a radical of the formula L—$NX^1X^2$, where L is $C_2$–$C_8$-alkylene and $X^1$ and $X^2$ independently of one another are each $C_1$–$C_6$-alkyl or, together with the nitrogen atom linking them, form a 5-membered or 6-membered saturated heterocyclic radical which may furthermore contain an oxygen atom in the ring,
  $R^3$, $R^4$, $R^5$, $R^6$ and $R^7$ independently of one another are each hydrogen, $C_1$–$C_{15}$-alkyl or $C_1$–$C_{15}$-alkoxy and
  $R^8$ is hydrogen, $C_1$–$C_{15}$-alkyl, $C_1$–$C_{15}$-alkoxy, cyano, nitro or a radical of the formula $COOX^3$, where $X^3$ is hydrogen, $C_1$–$C_{15}$-alkyl which may be interrupted by from 1 to 4 ether oxygen atoms, or is a radical of the formula L—$NX^1X^2$, where L, $X^1$ and $X^2$ each have the abovementioned meanings, as pH-dependent markers for hydrocarbons, hydrocarbons containing the abovementioned azo dyes, a process for detecting these azo dyes in hydrocarbons and novel azo dyes.

DISCUSSION OF THE BACKGROUND

U.S. Pat. No. 5,145,573, U.S. Pat. No. 5,182,372 and EP-A-499 845 disclose azo dyes which serve as markers for mineral oils. However, it has been found that the dyes described there exhibit insufficient dilutability in hydrocarbons.

U.S. Pat. No. 4,009,008 furthermore describes a process for marking mineral oils by means of azo dyes, in which the dye added to the mineral oil is rendered visible by adding to the marked mineral oil an adsorbent which binds other colored components of the mineral oil.

It is an object of the present invention to provide novel markers for hydrocarbons. The novel markers should be easily obtainable and readily soluble in hydrocarbons. Moreover, they should be detectable in a simple manner. Even very small amounts of marker should be capable of being rendered visible by a strong color reaction.

SUMMARY OF THE INVENTION

We have found that this object is achieved and that the azo dyes of the formula I which are defined at the outset can advantageously be used as pH-dependent markers for hydrocarbons.

DETAILED DESCRIPTION OF THE PREFERRED EMBODIMENTS

All alkyl and alkylene radicals occurring in the formula stated here may be either straight-chain or branched.

If $X^1$ and $X^2$, together with the nitrogen atom linking them, form a 5-membered or 6-membered saturated heterocyclic radical which may furthermore contain an oxygen atom in the ring, examples of said radicals which are suitable are pyrrolidinyl, piperidinyl and morpholinyl.

$R^1$, $R^2$, $R^3$, $R^4$, $R^5$, $R^6$, $R^7$, $R^8$, $X^1$, $X^2$ and $X^3$ are, for example, methyl, ethyl, propyl, isopropyl, butyl, isobutyl, sec-butyl, pentyl, isopentyl, neopentyl, tert-pentyl, hexyl or 2-methylpentyl.

$R^1$, $R^2$, $R^3$, $R^4$, $R^5$, $R^6$, $R^7$, $R^8$ and $X^3$ are furthermore, for example, heptyl, octyl, 2-ethylhexyl, isooctyl, nonyl, isononyl, decyl, isodecyl, undecyl, dodecyl, tridecyl, 3,5,5,7-tetramethylnonyl, isotridecyl, tetradecyl or pentadecyl (the above names isooctyl, isononyl, isodecyl and isotridecyl are trivial names and originate from the alcohols obtained by the oxo synthesis; cf. Ullmann's Encyclopedia of Industrial Chemistry, 5th Edition, Vol. A1, pages 290 to 293, and Vol. A 10, pages 284 and 285).

$R^3$, $R^4$, $R^5$, $R^6$, $R^7$ and $R^8$ are furthermore, for example, methoxy, ethoxy, propoxy, isopropoxy, butoxy, isobutoxy, sec-butoxy, pentyloxy, isopentyloxy, neopentyloxy, tert-pentyloxy, hexyloxy, 2-methylpentyloxy, heptyloxy, octyloxy, 2-ethylhexyloxy, isooctyloxy, nonyloxy, isononyloxy, decyloxy, isodecyloxy, undecyloxy, dodecyloxy, tridecyloxy, 3,5,5,7-tetramethylnonyloxy, isotridecyloxy, tetradecyloxy or pentadecyloxy.

L is, for example, $(CH_2)_2$, $(CH_2)_3$, $(CH_2)_4$, $(CH_2)_5$, $(CH_2)_6$, $(CH_2)_7$, $(CH_2)_8$, $CH(CH_3)CH_2$ or $CH(CH_3)CH(CH_3)$.

$R^1$, $R^2$ and $X^3$ are furthermore, for example, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- or 4-butoxybutyl, 4,8-dioxadecyl, 4,7-dioxaundecyl, 3,6,9-trioxadecyl, 3,6,9-trioxaundecyl, 3,6,9-trioxadodecyl, 4,7,10-trioxaundecyl, 3,6,9,12-tetraoxatridecyl or 3,6,9,12-tetraoxatetradecyl.

Azo dyes of the formula Ia

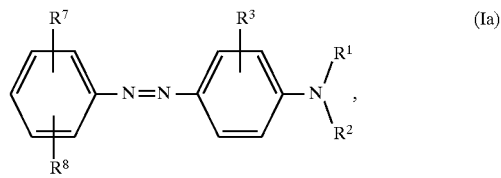

where
  $R^1$ is hydrogen or $C_1$–$C_{15}$-alkyl,
  $R^2$ and $R^3$ independently of one another are each $C_1$–$C_{15}$-alkyl and
  $R^7$ and $R^8$ each have the abovementioned meanings,
are preferably used for marking hydrocarbons.

Azo dyes of the formula Ib

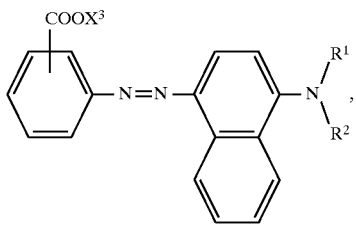

(Ib)

where
$R^1$ is hydrogen or $C_1$–$C_{15}$-alkyl,
$R^2$ is $C_1$–$C_{15}$-alkyl and
$X^3$ has the abovementioned meanings,
are furthermore preferably used for marking hydrocarbons.

Azo dyes of the formula Ic

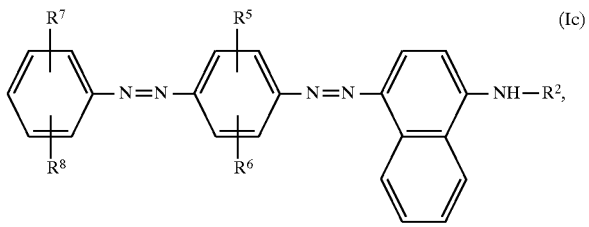

(Ic)

where
$R^2$ is $C_1$–$C_{15}$-alkyl and
$R^5$, $R^6$, $R^7$ and $R^8$ each have the abovementioned meanings, are also preferably used for marking hydrocarbons.

Azo dyes of the formula Ia, where $R^1$ and $R^2$ independently of one another are each $C_1$–$C_{13}$-alkyl, $R^3$ is methyl, $R^7$ is hydrogen and $R_8$ is a radical of the formula $COOX^3$, where $X^3$ is $C_1$–$C_{13}$-alkyl, are particularly preferably used for marking hydrocarbons.

Azo dyes of the formula Ic, where $R^2$ is $C_1$–$C_{13}$-alkyl, $R^5$ and $R^7$ are each methyl and $R^6$ and $R^8$ are each hydrogen, are furthermore particularly preferably used for marking hydrocarbons.

Some of the dyes of the formula I are known and are described, for example, in GB-A-953 719, U.S. Pat. No. 3,218,309 or U.S. Pat. No. 4,037,007.

For the purposes of the present invention, pH-dependent markers are to be understood as meaning those azo dyes of the formula I which, under the action of a protic acid, in the presence or absence of a halide of the metals zinc, aluminum or tin, give a color reaction, ie. a color change, accompanied by a deepening of color.

For the purposes of the present invention, marking is to be understood as meaning the addition of the azo dyes of the formula I to hydrocarbons in concentrations such that the hydrocarbons appear to the human eye to have either no color at all or only a slight color, but the dyes of the formula I are readily detectable in a clearly visible manner by the detection methods described in detail here.

The present invention furthermore relates to hydrocarbons containing one or more of the azo dyes of the formula I.

For the purposes of the present invention, hydrocarbons are to be understood as meaning aliphatic or aromatic hydrocarbons which are in the liquid state under standard conditions of temperature and pressure. These are in particular mineral oils, for example fuels, such as gasoline, kerosine or diesel oil, or oils, such as heating oil or motor oil.

The azo dyes of the formula I are suitable in particular for marking mineral oils which have to be identified, for example for tax reasons. In order to keep the costs of the identification low, it is desirable to use very small amounts of markers.

The azo dyes of the formula I, either in the absence of solvent or in the form of solutions, are used for marking hydrocarbons. Suitable solvents are organic solvents. Aromatic hydrocarbons, such as toluene, xylene, dodecylbenzene, diisopropylnaphthalene or a mixture of higher aromatics which is commercially available under the name Shellsol® AB (from Shell), are preferably used. In order to avoid a high viscosity of the resulting solutions, in general a concentration of azo dye I of from 20 to 80% by weight, based on the solution, is chosen.

Further cosolvents, for examples alcohols, such as methanol, ethanol, propanol, isopropanol, butanol, isobutanol, pentanol, hexanol, heptanol, octanol, 2-ethylhexanol or cyclohexanol, glycols, such as butylethylene glycol or methylpropylene glycol, amines, such as triethylamine, diisooctylamine, dicyclohexylamine, aniline, N-methylaniline, N,N-dimethylaniline, toluidine or xylidine, alkanolamines, such as 3-(2-methoxyethoxy) propylamine, o-cresol, m-cresol or p-cresol, ketones, such as diethylketone or cyclohexanone, lactams, such as γ-butyrolactam, carbonates, such as ethylene carbonate or propylene carbonate, phenols, such as tert-butylphenol or nonylphenol, esters, such as methyl phthalate, ethyl phthalate, 2-ethylhexyl phthalate, ethyl acetate, butyl acetate or cyclohexyl acetate, amides, such as N,N-dimethylformamide, N,N-diethylacetamide or N-methylpyrrolidone, or mixtures thereof, may be used for improving the solubility.

By means of the azo dyes of the formula I which are to be used according to the invention, it is possible in a very simple manner to detect marked hydrocarbons, even when the marking substances are present only in a concentration of about 10 ppm or less.

In some cases, it is also advantageous to use mixtures of dyes of the formula I with one another as marking substances.

The presence of the azo dyes of the formula I, used as markers, in hydrocarbons is advantageously detected if the hydrocarbon is treated with an aqueous alcoholic or alcoholic medium which contains a protic acid and, if required, a halide of the metals zinc, aluminum or tin. When aqueous alcoholic media are used, the weight ratio of water to alcohol is from 0.5:1 to 4:1, preferably about 1:1.

When the protic acid and, if required, the metal halide are added to the marked hydrocarbon, a clearly visible color reaction results and, in the case of the use of an aqueous alcoholic medium, the azo dye I passes over into the aqueous alcoholic phase.

Examples of suitable alcohols are ethanol, propanol, isopropanol, 1-methoxypropan-2-ol, ethylene glycol and 1,2- and 1,3-propylene glycol. The use of ethanol is preferred.

Suitable protic acids for the novel process are in particular strong acids, ie. protic acids whose pKa value is ≦3.5. Examples of suitable acids of this type are inorganic or organic acids, such as perchloric acid, hydriodic acid, hydrochloric acid, hydrobromic acid, hydrofluoric acid, sulfuric acid, nitric acid, phosphoric acid, benzenesulfonic acid, toluenesulfonic acid, naphthalenesulfonic acid, methanesulfonic acid, oxalic acid, maleic acid, chloroacetic acid, dichloroacetic acid and bromoacetic acid. In some cases, it may be advantageous to buffer these acids, for example by adding acetic acid.

In addition to o- or p-toluenesulfonic acid, inorganic acids are particularly noteworthy, hydrochloric acid or sulfuric acid being especially important.

Suitable halides of the metals zinc, aluminum or tin are, for example, zinc chloride, zinc bromide, aluminum chloride, aluminum bromide or tin tetrachloride. Zinc chloride is particularly noteworthy.

As a rule, it is sufficient to extract an amount of from about 10 to 50 ml of the hydrocarbon marked according to the invention with from 10 to 50 ml of an aqueous alcoholic or alcoholic solution of a protic acid, with or without the addition of the metal halide, in order to obtain this color reaction. It is also possible to use an aqueous alcoholic solution of the metal halide alone, since this is likewise acidic.

The concentration of the protic acid in the aqueous alcoholic or alcoholic solution is as a rule from 5 to 50, preferably from 10 to 30, % by weight. The concentration of metal halide is in general from 0 to 50, preferably from 5 to 20, % by weight, based on each case on the weight of the solution.

The present invention furthermore relates to azo dyes of the formula II

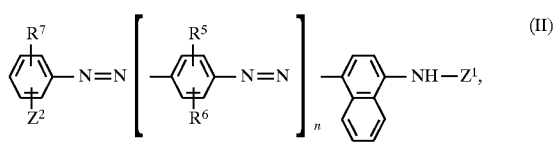

where
n is 0 or 1
and, when n is 0,
  $Z^1$ is $C_1$–$C_{15}$-alkyl which may be interrupted by from 1 to 4 ether oxygen atoms, or is a radical of the formula L—$NX^1X^2$, where L is $C_2$–$C_8$-alkylene and $X^1$ and $X^2$ independently of one another are each $C_1$–$C_6$-alkyl or, together with the nitrogen atom linking them, form a 5-membered or 6-membered saturated heterocyclic radical which may furthermore contain an oxygen atom in the ring,
  $R^7$ is hydrogen, $C_1$–$C_{15}$-alkyl or $C_1$–$C_{15}$-alkoxy and
  $Z^2$ is a radical of the formula $COOZ^3$, where $Z^3$ is $C_1$–$C_{15}$-alkyl which may be interrupted by from 1 to 4 ether oxygen atoms, or is a radical of the formula L—$NX^1X^2$, where L, $X^1$ and $X^2$ each have the abovementioned meanings,
with the proviso that, when $Z^1$ is L—$NX^1X^2$, the sum of the carbon atoms present in the radicals $X^1$, $X^2$ and $Z^3$ is at least 8,
or, when n is 1,
  $Z^1$ is a radical of the formula L—$NX^1X^2$, where L, $X^1$ and $X^2$ each have the abovementioned meanings, and
  $R^5$, $R^6$, $R^7$ and $Z^2$ are each hydrogen, $C_1$–$C_{15}$-alkyl or $C_1$–$C_{15}$-alkoxy,
with the proviso that, in each of the pairs of radicals $R^5/R^6$ and $R^7/Z^2$, one radical is not hydrogen.

The present invention furthermore relates to azo dyes of the formula III

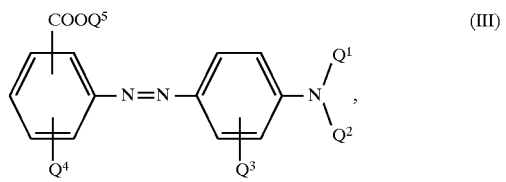

where
  $Q^1$ is hydrogen or $C_1$–$C_{15}$-alkyl,
  $Q^2$ is $C_1$–$C_{15}$-alkyl,
  $Q^3$ is $C_1$–$C_{15}$-alkyl or $C_1$–$C_{15}$-alkoxy,
  $Q^4$ is $C_1$–$C_{15}$-alkyl or $C_1$–$C_{15}$-alkoxy and
  $Q^5$ is $C_1$–$C_{15}$-alkyl which may be interrupted by from 1 to 4 ether oxygen atoms, or is a radical of the formula L—$NX^1X^2$, where L is $C_2$–$C_8$-alkylene and $X^1$ and $X^2$ independently of one another are each $C_1$–$C_6$-alkyl or, together with the nitrogen atom linking them, form a 5-membered or 6-membered saturated heterocyclic radical which may furthermore contain an oxygen atom in the ring, with the proviso that the sum of the carbon atoms present in the radicals $Q^1$, $Q^2$ and $Q^5$ is at least 8.

Azo dyes of the formula II where n is 0 are preferred.

Azo dyes of the formula II, where n is 0, $Z^1$ is $C_1$–$C_{13}$-alkyl, $R^7$ is hydrogen and $Z^2$ is $COOZ^3$, where $Z^3$ has the abovementioned meanings, are particularly preferred.

Azo dyes of the formula III, where $Q^1$, $Q^2$ and $Q^3$ independently of one another are each $C_1$–$C_{15}$-alkyl and $Q^4$ is hydrogen, are also preferred.

Azo dyes of the formula III, where $Q^1$ and $Q^2$ independently of one another are each $C_1$–$C_{13}$-alkyl, $Q^3$ is methyl, $Q^4$ is hydrogen and $Q^5$ is $C_1$–$C_{13}$-alkyl, are also particularly preferred.

The novel dyes of the formulae II and III can be obtained by methods known per se.

For the preparation of the dyes of the formula II, for example, an amine of the formula IVa or IVb

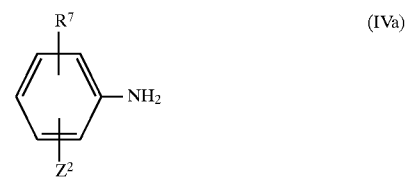

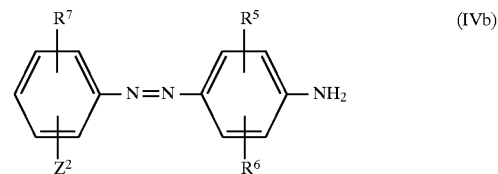

where $R^5$, $R^6$, $R^7$ and $Z^2$ each have the abovementioned meanings, can be diazotized in a manner known per se and the product coupled with a coupling component of the formula V

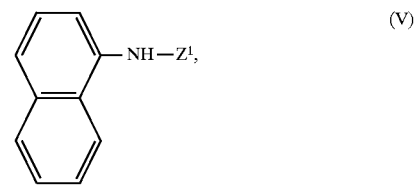

where $Z^1$ has the abovementioned meanings.

The amines of the formula IVb in turn are obtainable by diazotizing an amine of the formula IVa and then coupling the product with an aniline of the formula IVc

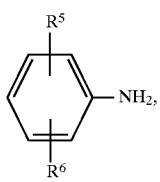

where $R^5$ and $R^6$ each have the abovementioned meanings.

For the preparation of the dyes of the formula III, for example, an amine of the formula VI

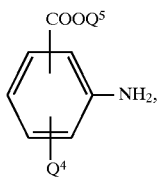

where $Q^4$ and $Q^5$ each have the abovementioned meanings, can be diazotized in a manner known per se and the product coupled with a coupling component of the formula VII

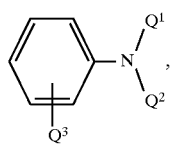

where $Q^1$, $Q^2$ and $Q^3$ each have the abovementioned meanings.

The novel azo dyes of the formulae II and III have good solubility in organic solvents and, as stated above, can advantageously be used as pH-dependent markers for hydrocarbons.

The examples which follow illustrate the invention.

A) Preparation

EXAMPLE 1

107 g of 4-(3'-methylphenylazo)-3-methylaniline hydrochloride and 0.5 g of a anionic surfactant were suspended in a mixture of 50 ml of water and 30 ml of 5N hydrochloric acid at room temperature. 50 g of ice and 20 ml of toluene were added, after which a concentrated aqueous solution of 6.9 g of sodium nitrite was introduced. The diazotization was completed in the course of 2 hours at from 5° to 10° C., after which the excess nitrite was removed using amidosulfonic acid. In order to dissolve the diazonium salt, a solution of 29.5 g of 1-(3-diethylaminopropyl)aminonaphthalene in 35 ml of toluene was then added dropwise at from 10° to 15° C. Thereafter, the pH of the reaction mixture was increased to about 4 with 2.5N sodium acetate solution, and the coupling was complete after 30 minutes. After the pH had been increased to about 8 with 10N sodium hydroxide solution, phase separation occurred. The organic phase was then washed salt-free at 60° C. by extracting several times with water. Distilling off the toluene gave 50 g of an oil-like dye of the formula

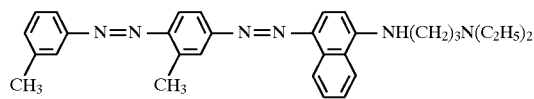

which readily dissolves in aromatics to give a red solution. $\lambda_{max}$(toluene): 522 nm.

EXAMPLE 2

35.2 g of a 58% strength by weight aqueous solution of 2-dimethylaminoethyl anthranilate were added dropwise to a mixture of 33 ml of 10N hydrochloric acid and 10 ml of glacial acetic acid at from 5° to 10° C. A concentrated aqueous solution of 6.9 g of sodium nitrite was then added at from 10° to 15° C., the pH being kept below 0.5. The diazotization was complete in the course of 30 minutes at from 10° to 15° C., after which the excess nitrite was removed using amidosulfonic acid. 1 g of an anionic surfactant was added, after which 26.2 g of 1-(2-ethylhexylamino)naphthalene, dissolved in 30 ml of glacial acetic acid, were added dropwise to the solution of the diazonium salt at from 10° to 15° C. in the course of 30 minutes. Thereafter, the batch was diluted with 100 ml of water, and the coupling was complete after 2 hours. After 100 ml of toluene had been added and the pH increased to about 7 with 10N sodium hydroxide solution, phase separation occurred. The organic phase was then washed salt-free at 60° C. by extracting several times with water. Distilling off the toluene gave 48 g of an oil-like dye of the formula

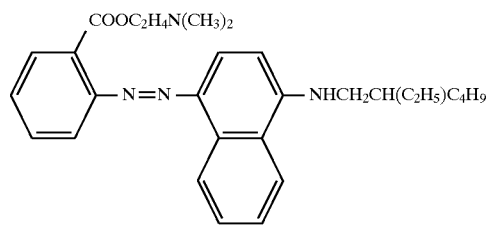

which readily dissolved in aromatics to give an orange solution. $\lambda_{max}$(toluene): 448 nm.

B) Use

General method

A 40% strength by weight solution of the marker in a commercial mixture of higher aromatics (Shellsol® AB from Shell) is added to commercial diesel fuel.

The amount of marker added is 10 ppm.

a) 50 ml of an acidic test solution consisting of 45 g of water, 45 g of ethanol, 5 g of p-toluenesulfonic acid and 5 g of zinc chloride are added to 50 ml of marked diesel fuel in a separating funnel. The mixture is vigorously shaken for about 10 seconds. After the phases have separated again, the test solution phase is found to have an intense color. The aqueous phase can be measured photometrically against a solution of known concentration.

b) 20 ml of marked diesel fuel are vigorously shaken with 20 ml of reagent solution (10% strength by weight zinc chloride solution in a water/ethanol mixture (60:40 v/v), pH brought to 2 by adding 85% strength by weight acetic acid). The lower, aqueous phase acquires a clearly detectable color. The aqueous phase can be measured photometrically against a solution of known concentration.

The dyes shown in the tables below were detected by method a). They can also be detected just as successfully by method b).

In the tables below, the $\lambda_{max}$ values indicated by *) were each measured in toluene, and the $\lambda_{max}$ values indicated by **) were each measured in water:ethanol:p-toluenesulfonic acid:zinc chloride 45:45:5:5 (w/w/w/w).

TABLE 1

[Structure: benzene ring with COOK¹ substituent, N=N azo linkage to naphthalene with NH—K² substituent]

| Ex. No. | K¹ | K² | $\lambda_{max}^{*)}$ [nm] | $\lambda_{max}^{**)}$ [nm] |
|---|---|---|---|---|
| 3 | CH₃ | C₂H₅ | 447 | 539 |
| 4 | CH₂CH(C₂H₅)C₄H₉ | C₂H₅ | 444 | 540 |
| 5 | CH₂CH(C₂H₅)C₄H₉ | CH₂CH(C₂H₅)C₄H₉ | 445 | 543 |
| 6 | CH₃ | (CH₂)₃O(CH₂)₂OCH₃ | 454 | 540 |
| 7 | CH₂CH(C₂H₅)C₄H₉ | (CH₂)₂—N(morpholino) | 454 | 554 |
| 8 | CH₂CH(C₂H₅)C₄H₉ | (CH₂)₃—N(C₂H₅)₂ | 458 | 544 |
| 9 | (CH₂)₂—N(CH₃)₂ | C₂H₅ | 447 | 540 |
| 10 | CH₃ | CH₂CH(C₂H₅)C₄H₉ | 446 | 542 |
| 11 | CH₂CH(C₂H₅)C₄H₉ | (CH₂)₂—N(iso-C₃H₇)₂ | 450 | 554 |
| 12 | (CH₂)₂—N(CH₃)₂ | iso-C₁₃H₂₇ | 448 | 544 |
| 13 | CH₂CH(C₂H₅)C₄H₉ | (CH₂)₂—N(C₄H₉)₂ | 448 | 552 |
| 14 | CH₂CH(C₂H₅)C₄H₉ | (CH₂)₃—N(piperidino) | 460 | 546 |

TABLE 2

[Structure: benzene ring with COOK¹, N=N azo linkage to benzene with CH₃ and N(K²)(K³)]

| Ex. No. | K¹ | K² | K³ | $\lambda_{max}^{*)}$ [nm] | $\lambda_{max}^{**)}$ [nm] |
|---|---|---|---|---|---|
| 15 | CH₃ | C₂H₅ | C₂H₅ | 425 | 519 |
| 16 | CH₂CH(C₂H₅)C₄H₉ | C₂H₅ | C₂H₅ | 422 | 518 |
| 17 | (CH₂)₂—N(CH₃)₂ | C₂H₅ | C₂H₅ | 424 | 520 |

TABLE 3

[Structure: bis-azo with tolyl—N=N—(methylphenyl)—N=N—naphthyl—NH—K]

| Ex. No. | K | $\lambda_{max}^{*)}$ [nm] | $\lambda_{max}^{**)}$ [nm] |
|---|---|---|---|
| 18 | (CH₂)₂—N(morpholino) | 513 | 582 |
| 19 | (CH₂)₃—N(C₂H₅)₂ | 512 | 592 |
| 20 | C₂H₅ | 507 | 579 |
| 21 | CH₂CH(C₂H₅)C₄H₉ | 504 | 582 |
| 22 | mixture (1:1) of CH₂CH(C₂H₅)C₄H₉ and isotridecyl | 506 | 582 |
| 23 | (CH₂)₃O(CH₂)₂OCH₃ | 514 | 582 |
| 24 | (CH₂)₃O(CH₂)₂OC₄H₉ | 515 | 582 |
| 25 | mixture (1:1) of (CH₂)₃O(CH₂)₂OCH₃ and (CH₂)₃O(CH₂)₂OC₄H₉ | 514 | 578 |
| 26 | (CH₂)₃O(CH₂)₂O(CH₂)₂OCH₃ | 514 | 580 |
| 27 | (CH₂)₂—N(C₄H₉)₂ | 509 | 592 |
| 28 | (CH₂)₃—N(piperidino) | 520 | 584 |
| 29 | iso-C₁₃H₂₇ | 503 | 580 |

TABLE 4

[Structure: benzene with K¹, K² substituents, N=N linkage to naphthalene with NH—K³]

| Ex. No. | K¹ | K² | K³ | $\lambda_{max}^{*)}$ [nm] | $\lambda_{max}^{**)}$ [nm] |
|---|---|---|---|---|---|
| 30 | H | OCH₃ | C₂H₅ | 447 | 565 |
| 31 | CH₃O | H | C₂H₅ | 439 | 582 |
| 32 | CH₃O | H | CH₂CH(C₂H₅)C₄H₉ | 440 | 588 |
| 33 | CH₃O | H | (CH₂)₃O(CH₂)₂OCH₃ | 445 | 585 |
| 34 | CH₃O | H | mixture (1:1) of (CH₂)₃O(CH₂)₂OCH₃ and (CH₂)₃O(CH₂)₂OC₄H₉ | 444 | 584 |
| 35 | C₂H₅O | H | (CH₂)₃O(CH₂)₂OCH₃ | 445 | 587 |
| 36 | C₂H₅O | H | (CH₂)₃O(CH₂)₂OC₄H₉ | 444 | 588 |

TABLE 5

[Structure with K¹, K², K³ on first ring, N=N linker, second ring with CH₃ and N(K⁴)(K⁵)]

| Ex. No. | K¹ | K² | K³ | K⁴ | K⁵ | λ_max*) [nm] | λ_max**) [nm] |
|---|---|---|---|---|---|---|---|
| 37 | 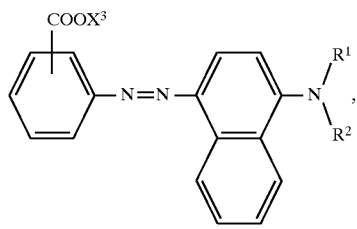 | H | CH₃ | C₂H₅ | C₂H₅ | 482 | 558 |
| 38 | CH₃O | H | H | C₂H₅ | C₂H₅ | 418 | 555 |

We claim:

1. A method of marking a hydrocarbon, comprising adding to a hydrocarbon an azo dye of the formula Ib

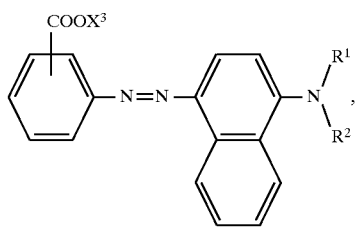

where $R^1$ is hydrogen or $C_1$–$C_{15}$-alkyl, $R^2$ is $C_1$–$C_{15}$-alkyl and $X^3$ is hydrogen, $C_1$–$C_{15}$-alkyl which is uninterrupted or interrupted by from 1 to 4 ether oxygen atoms or is a radical of the formula $LNX^1X^2$, where L is $C_2$–$C_8$-alkylene and $X^1$ and $X^2$ independently of one another are each $C_1$–$C_6$-alkyl or, together with the nitrogen atom linking them, form a 5-membered or 6-membered saturated heterocyclic radical which does or does not furthermore contain an oxygen atom in the ring.

2. A hydrocarbon containing one or more azo dyes, as pH-dependent markers, of the formula Ib where $R^1$ is hydrogen or $C_1$–$C_{15}$-alkyl, $R^2$ is $C_1$–$C_{15}$-alkyl and $X^3$ is hydrogen, $C_1$–$C_{15}$-alkyl which is uninterrupted or interrupted by from 1 to 4 ether oxygen atoms or is a radical of the formula $LNX^1X^2$, where L is $C_2$–$C_8$-alkylene and $X^1$ and $X^2$ independently of one another are each $C_1$–$C_6$-alkyl or, together with the nitrogen atoms linking them, form a 5-membered or 6-membered saturated heterocyclic radical which does or does not furthermore contain an oxygen atom in the ring.

* * * * *